(12) United States Patent
Whitmore (10) Patent No.: US 11,220,470 B2
(45) Date of Patent: *Jan. 11, 2022

(54) SYSTEM AND PROCESS FOR RECOVERING METHANE AND CARBON DIOXIDE FROM BIOGAS AND REDUCING GREENHOUSE GAS EMISSIONS

(71) Applicant: WM Intellectual Property Holdings, L.L.C., Houston, TX (US)

(72) Inventor: Noah Whitmore, Houston, TX (US)

(73) Assignee: WM INTELLECTUAL PROPERTY HOLDINGS, L.L.C., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/221,462

(22) Filed: Apr. 2, 2021

(65) Prior Publication Data

US 2021/0221755 A1    Jul. 22, 2021

Related U.S. Application Data

(63) Continuation of application No. 17/035,411, filed on Sep. 28, 2020, now Pat. No. 10,968,151.

(Continued)

(51) Int. Cl.
*C07C 7/11* (2006.01)
*C07C 7/12* (2006.01)
(Continued)

(52) U.S. Cl.
CPC .......... *C07C 7/005* (2013.01); *B01D 53/0446* (2013.01); *B01D 53/0462* (2013.01);
(Continued)

(58) Field of Classification Search
None
See application file for complete search history.

(56) References Cited

U.S. PATENT DOCUMENTS

| 4,270,937 A | 6/1981 | Adler et al. |
| 4,681,612 A | 7/1987 | O'Brien et al. |

(Continued)

FOREIGN PATENT DOCUMENTS

| DE | 3639779 | 6/1988 |
| FR | 2928720 | 9/2009 |

(Continued)

OTHER PUBLICATIONS

Finn, Adrian J. et al.; Processing of Carbon Dioxide Rich Gas, Sep. 17, 2014; 18 pages; Costain Group PLC.

(Continued)

*Primary Examiner* — Tam M Nguyen
(74) *Attorney, Agent, or Firm* — Greenberg Traurig LLP (57) ABSTRACT

Various illustrative embodiments of a system and process for recovering high-quality biomethane and carbon dioxide product streams from biogas sources and utilizing or sequestering the product streams are provided. The system and process synergistically yield a biomethane product which meets gas pipeline quality specifications and a carbon dioxide product of a quality and form that allows for its transport and sequestration or utilization and reduction in greenhouse gas emissions. The system and process result in improved access to gas pipelines for products, an improvement in the carbon intensity rating of the methane fuel, and improvements in generation of credits related to reductions in emissions of greenhouse gases.

13 Claims, 1 Drawing Sheet

Related U.S. Application Data (60) Provisional application No. 62/907,348, filed on Sep. 27, 2019.

(51) Int. Cl.

| | | |
|---|---|---|
| *C07C 7/00* | (2006.01) | |
| *C01B 32/50* | (2017.01) | |
| *B01D 53/04* | (2006.01) | |
| *B01D 53/14* | (2006.01) | |
| *B01D 53/22* | (2006.01) | |
| *B01D 53/26* | (2006.01) | |
| *B01D 53/86* | (2006.01) | |
| *C10L 1/04* | (2006.01) | |
| *G06Q 10/00* | (2012.01) | |
| *G06Q 30/00* | (2012.01) | |
| *G06Q 40/00* | (2012.01) | |
| *G06Q 50/06* | (2012.01) | |
| *G06Q 40/04* | (2012.01) | |

(52) U.S. Cl.
CPC ..... *B01D 53/1425* (2013.01); *B01D 53/1475* (2013.01); *B01D 53/1493* (2013.01); *B01D 53/229* (2013.01); *B01D 53/261* (2013.01); *B01D 53/265* (2013.01); *B01D 53/864* (2013.01); *B01D 53/8671* (2013.01); *C01B 32/50* (2017.08); *C07C 7/11* (2013.01); *C07C 7/12* (2013.01); *C10L 1/04* (2013.01); *G06Q 10/30* (2013.01); *G06Q 30/018* (2013.01); *G06Q 40/10* (2013.01); *G06Q 50/06* (2013.01); *B01D 2252/10* (2013.01); *B01D 2252/204* (2013.01); *B01D 2253/116* (2013.01); *B01D 2255/102* (2013.01); *B01D 2256/22* (2013.01); *B01D 2256/245* (2013.01); *B01D 2257/102* (2013.01); *B01D 2257/104* (2013.01); *B01D 2257/108* (2013.01); *B01D 2257/206* (2013.01); *B01D 2257/502* (2013.01); *B01D 2257/708* (2013.01); *B01D 2257/80* (2013.01); *C10L 2290/08* (2013.01); *C10L 2290/541* (2013.01); *C10L 2290/542* (2013.01); *C10L 2290/60* (2013.01); *F25J 2215/42* (2013.01); *G06Q 40/04* (2013.01)

(56) References Cited

U.S. PATENT DOCUMENTS

| | | |
|---|---|---|
| 4,762,543 A | 8/1988 | Pantermuehl et al. |
| 5,021,232 A | 6/1991 | Hise et al. |
| 5,642,630 A | 7/1997 | Abdelmalek et al. |
| 5,681,360 A | 10/1997 | Siwajek et al. |
| 5,842,357 A | 12/1998 | Siwajek et al. |
| 5,927,103 A | 7/1999 | Howard |
| 5,974,829 A | 11/1999 | Novak et al. |
| 6,082,133 A * | 7/2000 | Barclay ................. F25J 1/0042 62/619 |
| 7,594,414 B2 | 9/2009 | Wilding et al. |
| 7,915,379 B2 | 3/2011 | Turner et al. |
| 8,557,024 B2 | 10/2013 | Reddy et al. |
| 10,222,121 B2 | 3/2019 | Cullinane et al. |
| 10,254,042 B2 | 4/2019 | Higginbotham et al. |
| 10,273,046 B2 | 4/2019 | Whitman et al. |
| 10,968,151 B1 | 4/2021 | Whitmore |
| 2005/0080520 A1 | 4/2005 | Kline et al. |
| 2005/0287056 A1 | 12/2005 | Baker et al. |
| 2011/0000402 A1 | 1/2011 | Grasso, Jr. |
| 2011/0003357 A1* | 1/2011 | Barclay ................. C12M 23/58 435/167 |
| 2011/0185896 A1 | 8/2011 | Sethna et al. |
| 2011/0265647 A1 | 11/2011 | Find et al. |
| 2016/0003532 A1 | 1/2016 | Young et al. |
| 2017/0102182 A1* | 4/2017 | Tremblay ............... F25J 3/0257 |
| 2017/0107478 A1* | 4/2017 | Harmon .................. F23J 15/02 |
| 2017/0158503 A1* | 6/2017 | Foody ....................... C10L 1/04 |
| 2017/0227285 A1 | 8/2017 | Find |
| 2017/0304769 A1 | 10/2017 | Bigeard et al. |
| 2018/0016096 A1 | 1/2018 | Krishnamurthy et al. |
| 2019/0130560 A1 | 5/2019 | Horowitz et al. |
| 2019/0185887 A1* | 6/2019 | Foody ....................... C12P 7/10 |
| 2019/0210798 A1 | 7/2019 | Schultz |
| 2019/0279168 A1 | 9/2019 | Lardner |
| 2019/0304236 A1 | 10/2019 | Chan et al. |
| 2021/0094894 A1* | 4/2021 | Whitmore .......... B01D 53/1493 |

FOREIGN PATENT DOCUMENTS

| | | |
|---|---|---|
| WO | 2009/030877 | 3/2009 |
| WO | 2016/070237 | 5/2016 |
| WO | 2017/021003 | 2/2017 |
| WO | 2017/140662 | 8/2017 |

OTHER PUBLICATIONS

Carbon Dioxide Enhanced Oil Recovery, Untapped Domestic Energy Supply and Long Term Carbon Storage Solution; Mar. 2010; 32 pages; National Energy Technology Laboratory ("NETL").

Townsend, Alex et al.; The LCFS and CCS Protocol: An Overview for Policymakers and Project Developers; 2019; 24 pages; Global CCS Institute.

Mokhatab, Saeid et al.; Handbook of Natural Gas Transmission and Processing, Principles and Practices; Chapter 6.10 Cryogenic Fractionation; 2015; Elsevier Inc.; 20 pages.

Guidance Document for the Introduction of Landfill-Derived Renewable Gas into Natural Gas Pipelines; May 2, 2012; 43 pages; Gas Technology Institute.

Guidance Document for the Introduction of Landfill-Derived Renewable Gas into Natural Gas Pipelines, Appendix—Analytical Data; May 2, 2012; 135 pages; Gas Technology Institute.

Acrion Technologies, Inc.; Acrion—CO2 Wash; printed Oct. 14, 2019; 6 pages; www.environmental-expert.com/training/acrion-co2-wash-601175.

Petersson, Anneli et al.; Biogas Upgrading Technologies—Developments and Innovations; Oct. 2009; 20 pages; IEA Bioenergy.

Wegrzyn, James; Opportunities for Clean Fuels from Land Fill Gas; 2003; pp. 917-918; Prepr. Pap.-AM. Chem. Soc., Div. Fuel Chem; 48(2), US.

Ning, Al; Planning For Sustainable Material and Waste Management; May 2017; 48 pages; American Planning Association; US.

O'Connor, Mary Catherine; Dumpster Diving Robots: Using AI for Smart Recycling; Jul. 10, 2017; 6 pages; GE Reports.

Southern California Gas Company; Rule 30: Transportation of Customer-Owned Gas, Renewable Natural Gas Tool Kit; 2015; 32 pages.

Schafer, Manfred et al.; Adsorption and Desorption of Halogenated Hydrocarbons Using Activated Carbon; 1991; Chem. Eng. Technol; pp. 59-64.

Shepherd, Austin; Activated Carbon Adsorption for Treatment of VOC Emissions; May 2001; 4 pages.

European Patent Office; PCT Written Opinion of the International Searching Authority, issued in connection with PCT/US20/053143; dated Jan. 14, 2021; 6 pages; Europe.

European Patent Office; PCT International Search Report, issued in connection with PCT/US20/053143; dated Jan. 14, 2021; 5 pages; Europe.

\* cited by examiner ent. Capture and beneficial utilization, storage, or sequestration of the carbon dioxide portion of the biogas would lead to significant additional reductions in emissions of greenhouse gases.
SYSTEM AND PROCESS FOR RECOVERING METHANE AND CARBON DIOXIDE FROM BIOGAS AND REDUCING GREENHOUSE GAS EMISSIONS

RELATED APPLICATIONS

This application is a continuation application and claims the benefit, and priority benefit, of U.S. patent application Ser. No. 17/035,411, filed Sep. 28, 2020, now U.S. Pat. No. 10,968,151, which claims the benefit, and priority benefit, of U.S. Provisional Patent Application Ser. No. 62/907,348, filed Sep. 27, 2019, the disclosure and contents of which are incorporated by reference herein in their entirety.

BACKGROUND

Field of the Invention

The presently disclosed subject matter relates to recovery of biomethane and carbon dioxide product streams from biogas sources.

Description of the Related Art

Biogas is gas produced through the decomposition of organic matter in facilities such as solid waste landfills, wastewater treatment plants, or other anaerobic digesters. Biogas is composed primarily of methane and carbon dioxide, but also contains lesser amounts of other compounds. The gas is typically either flared to thermally destruct the combustible compounds or is beneficially utilized for its methane content. Typical beneficial use applications include combustion of the biogas for industrial heating applications, combustion of the biogas for electricity generation, or processing the biogas to generate a methane (biomethane) product that can be injected into natural gas pipelines or used in compressed natural gas (CNG) vehicle fuel applications. The beneficial use of biogas or biomethane typically leads to reductions in greenhouse gas emissions due to the displacement of carbon dioxide emissions associated with the use and combustion of conventional fossil natural gas. Regardless of whether the biogas is flared or beneficially utilized for the methane component, the carbon dioxide portion of the biogas is ordinarily released to atmosphere. Capture and beneficial utilization, storage, or sequestration of the carbon dioxide portion of the biogas would lead to significant additional reductions in emissions of greenhouse gases.

Municipal solid waste landfills are the largest generators and sources of biogas in the United States. Typical landfills in the United States produce around 800-8,000 SCFM of biogas. The composition and rate of production of the biogas is largely dependent on the fresh feed rate, existing volume, and composition of organic material; fresh feed rate, existing volume, and composition of other substances; operating temperature; moisture content; oxygen content; bacterial makeup; length of time spent digesting; and the design and operation of the digestion and gas extraction facilities. For example, the disposal of cosmetics and deodorants within household waste leads to siloxanes in the biogas, the presence of refrigerants leads to halogenated hydrocarbons in the biogas, and the operation of the landfill gas collection system under vacuum in an effort to limit fugitive emissions often incidentally leads to the presence of nitrogen and oxygen in the biogas. While the primary components of biogas are methane and carbon dioxide, the gas ordinarily also contains water vapor, nitrogen, and oxygen and can also contain less than one percent of various other contaminants such as hydrogen, carbon monoxide, ammonia, sulfur compounds, halogenated hydrocarbons, siloxanes, other volatile and semi-volatile organic compounds, and heavy metals. While some measures can be taken to segregate certain wastes and adjust extraction rates from certain wells to control biogas composition, the composition of biogas extracted from an active landfill varies significantly over time.

Biogas beneficial use applications which involve processing the gas to generate a biomethane product for injection into natural gas pipelines require that the biomethane product be sufficiently purified from compounds that may jeopardize the integrity of pipeline systems, lead to damage of downstream equipment, or would pose risks to human or environmental health. Prospective biogas processing facilities which would include the recovery of carbon dioxide would similarly require that the recovered carbon dioxide be of suitable quality for transport, utilization, storage, or sequestration. As such, there is a need to design advanced biogas processing facilities with sufficient robustness to handle a wide range of potential inlet gas compositions and contaminant levels while satisfying strict product purity requirements. Additionally, it is desirable that these processing facilities be designed to maximize the recovery of biomethane, maximize the recovery of carbon dioxide, and minimize overall emissions of greenhouse gases. It is most desirable to do these things simultaneously and synergistically.

Conventional methods of processing biogas for biomethane production involve separation of methane and other compounds within the gas stream by passing the gas stream through various combinations of single-use adsorbent or scavenger beds, pressure-swing adsorption (PSA) packages, temperature-swing adsorption (TSA) packages, membranes, physical solvent-based absorbers, and chemical solvent-based absorbers. These conventional processes have certain limitations including limitations on methane product purity and methane recovery rate. Despite the processing efforts, conventional methods can leave trace amounts of halogenated hydrocarbons, other volatile organic compounds, siloxanes, oxygen, nitrogen, hydrogen, and heavy metals in the product gas. Additionally, less than about 97% of the inlet methane is typically recovered in the product gas. Further, the carbon dioxide portion of the biogas is typically separated in a gaseous state along with other contaminants which impairs and prevents subsequent transport, utilization, or storage of the carbon dioxide. Because the transport, utilization, or storage of the carbon dioxide portion of the biogas is impaired under conventional processing techniques, reductions in overall emissions of greenhouse gases are limited and the carbon intensity of the methane fuel is typically limited to around 30-60 $gCO_2e/MJ$. While previous patents have attempted to present viable methods for recovering both biomethane and carbon dioxide from biogas, these teachings have failed to present the most efficient methods for processing biogas to maximize recovery of both biomethane and carbon dioxide products of adequate quality and form to enable any subsequent use.

Improvements in this field of technology are desired.

SUMMARY

Various illustrative embodiments of a system and process for recovering high-quality biomethane and carbon dioxide product streams from biogas sources and utilizing or sequestering the product streams are disclosed herein. The system and process synergistically yield a biomethane product which meets gas pipeline quality specifications and a carbon dioxide product of a quality and form that allows for its transport and sequestration or utilization and reduction in greenhouse gas emissions. The system and process result in improved access to gas pipelines for products, an improvement in the carbon intensity rating of the methane fuel, and improvements in generation of credits related to reductions in emissions of greenhouse gases. Additionally, the system and process are an improvement to the overall methane recovery efficiency for biogas processing facilities. The system and process include low temperature liquefaction of carbon dioxide from a biogas source to simultaneously purify the biomethane from contaminants and yield a marketable liquid carbon dioxide product; sequestering or supplying the biogas-derived carbon dioxide for sequestration or other utilization; utilizing or supplying the biomethane as compressed or liquefied fuel for vehicles, as process heat fuel, as feedstock for fuel or chemical synthesis, or as feedstock for hydrogen generation; and monitoring the material and energy inputs and outputs from the facility to verify reductions in greenhouse gas emissions.

In certain illustrative embodiments, a process for recovering methane and carbon dioxide from a biogas source for beneficial use or sequestration includes the steps of: (a) extracting at least one gas stream comprising a biogas from a biogas-generating facility; (b) compressing, cooling, and separating the gas stream from liquid water; (c) removing a majority of the trace contaminants from the gas stream; (d) removing oxygen from the gas stream to produce a deoxygenated gas stream; (e) drying the gas stream to reduce the water vapor content; (f) cooling the gas stream in a liquefaction unit to liquefy at least some of the contained carbon dioxide; (g) utilizing the liquid carbon dioxide as an absorbent to purify the gas stream; (h) separating any remaining gaseous carbon dioxide from the gas stream and recycling the gaseous carbon dioxide to a point upstream from the liquefaction unit such that the carbon dioxide contained in the gas stream is substantially separated and recovered as a liquid product; (i) separating nitrogen from the gas stream to produce a biomethane product stream; (j) sequestering or supplying the biogas-derived carbon dioxide product for sequestration or other utilization; (k) utilizing or supplying the biomethane product stream as compressed or liquefied fuel for vehicles, as process heat fuel, as feedstock for fuel or chemical synthesis, or as feedstock for hydrogen generation; and (l) monitoring the material and energy inputs and outputs from a biogas processing facility to determine reductions in greenhouse gas emissions, wherein at least some of the aforementioned steps (b)-(i) occur in the biogas processing facility. Air intrusion into the biogas can be controlled to achieve a minimum oxygen to hydrogen, carbon monoxide, and hydrogen sulfide ratio of 0.5. The separated nitrogen stream can be utilized to regenerate contaminant-laden adsorbent or absorbent. The contaminant-laden nitrogen stream can be transmitted to a thermal oxidizer or flare for thermal destruction of the contaminants. The overall methane recovery efficiency can be greater than 98%. The gross heating value of the biomethane product can be greater than 1,000 Btu/SCF. The carbon intensity of the biomethane can be less than 25 $gCO_2e/MJ$. The halogenated hydrocarbon level in the biomethane product stream can be less than 0.1 ppmv. The siloxane level in the biomethane product stream can be less than 0.01 mgSi/m3. The carbon dioxide can be sequestered through injection into an underground geologic reservoir. The reservoir can be monitored for verification of extended or permanent storage of carbon dioxide. The carbon dioxide can be sequestered through injection into an underground geologic reservoir for enhancement of oil recovery. The reservoir can be monitored for verification of extended or permanent storage of carbon dioxide. The carbon dioxide can be sequestered through reaction with another material to form carbonate minerals. The conversion of carbon dioxide to carbonates can be monitored for verification of sequestration. Credits can be generated due to the reduction in greenhouse gases.

In certain illustrative embodiments, a process for recovering methane and carbon dioxide from one or more biogas sources for beneficial use or sequestration includes the steps of: (a) extracting at least one gas stream comprising a biogas from a biogas-generating facility; (b) compressing, cooling, and separating the gas stream from liquid water; (c) removing a majority of the trace contaminants from the gas stream; (d) removing oxygen from the gas stream to produce a deoxygenated gas stream; (e) drying the gas to reduce the water vapor content; (f) cooling the gas stream in a liquefaction unit to liquefy at least some of the contained carbon dioxide; (g) utilizing the liquid carbon dioxide as an absorbent to purify the gas stream; (h) separating the remaining gaseous carbon dioxide from the gas stream to produce a biomethane product stream and recycling the gaseous carbon dioxide to a point upstream from the liquefaction unit such that the carbon dioxide contained in the biogas is substantially separated and recovered as a liquid product; (i) sequestering or supplying the biogas-derived carbon dioxide product for sequestration or other utilization; (j) utilizing or supplying the biomethane product stream as compressed or liquefied fuel for vehicles, as process heat fuel, as feedstock for fuel or chemical synthesis, or as feedstock for hydrogen generation; and (k) monitoring the material and energy inputs and outputs from a biogas processing facility to determine reductions in greenhouse gas emissions, wherein at least some of the aforementioned steps (b)-(h) occur in the biogas processing facility. The overall methane recovery efficiency can be greater than 98%. The gross heating value of the biomethane product can be greater than 1,000 Btu/SCF. The carbon intensity of the biomethane can be less than 25 $gCO_2e/MJ$. The halogenated hydrocarbon level in the biomethane product stream can be less than 0.1 ppmv. The siloxane level in the biomethane product stream can be less than 0.01 mgSi/m3. The carbon dioxide can be sequestered through injection into an underground geologic reservoir. The reservoir can be monitored for verification of extended or permanent storage of carbon dioxide. The carbon dioxide can be sequestered through injection into an underground geologic reservoir for enhancement of oil recovery. The reservoir can be monitored for verification of extended or permanent storage of carbon dioxide. The carbon dioxide can be sequestered through reaction with another material to form carbonate minerals. The conversion of carbon dioxide to carbonates can be monitored for verification of sequestration. Credits can be generated due to the reduction in greenhouse gases.

In certain illustrative embodiments, a process for recovering methane and carbon dioxide from one or more biogas sources for beneficial use or sequestration includes the steps of: (a) extracting at least one gas stream comprising a biogas from a biogas-generating facility; (b) compressing, cooling, and separating the gas stream from liquid water; (c) removing a majority of the trace contaminants from the gas stream; (d) drying the gas stream to reduce the water vapor content; (e) cooling the gas stream in a liquefaction unit to liquefy at least some of the contained carbon dioxide; (f) utilizing the liquid carbon dioxide as an absorbent to purify the gas stream; (g) separating the remaining gaseous carbon dioxide from the gas stream to produce a biomethane product stream and recycling the gaseous carbon dioxide to a point upstream from the liquefaction unit such that the carbon dioxide contained in the gas stream is substantially separated and recovered as a liquid product; (h) sequestering or supplying the biogas-derived carbon dioxide liquid product for sequestration or other utilization; (i) utilizing or supplying the biomethane product stream as compressed or liquefied fuel for vehicles, as process heat fuel, as feedstock for fuel or chemical synthesis, or as feedstock for hydrogen generation; and (j) monitoring the material and energy inputs and outputs from a biogas processing facility to determine reductions in greenhouse gas emissions, wherein at least some of the aforementioned steps (b)-(g) occur in the biogas processing facility. The overall methane recovery efficiency can be greater than 98%. The gross heating value of the biomethane product can be greater than 1,000 Btu/SCF. The carbon intensity of the biomethane can be less than 25 g$CO_2$e/MJ. The halogenated hydrocarbon level in the biomethane product stream can be less than 0.1 ppmv. The siloxane level in the biomethane product stream can be less than 0.01 mgSi/m3. The carbon dioxide can be sequestered through injection into an underground geologic reservoir. The reservoir can be monitored for verification of extended or permanent storage of carbon dioxide. The carbon dioxide can be sequestered through injection into an underground geologic reservoir for enhancement of oil recovery. The reservoir can be monitored for verification of extended or permanent storage of carbon dioxide. The carbon dioxide can be sequestered through reaction with another material to form carbonate minerals. The conversion of carbon dioxide to carbonates can be monitored for verification of sequestration. Credits can be generated due to the reduction in greenhouse gases.

BRIEF DESCRIPTION OF THE DRAWINGS

A better understanding of the presently disclosed subject matter can be obtained when the following detailed description is considered in conjunction with the drawings and FIGS herein, wherein.

While the presently disclosed subject matter will be described in connection with the preferred embodiment, it will be understood that it is not intended to limit the presently disclosed subject matter to that embodiment. On the contrary, it is intended to cover all alternatives, modifications, and equivalents, as may be included within the spirit and the scope of the presently disclosed subject matter as defined by the appended claims.

DETAILED DESCRIPTION

The presently disclosed subject matter relates to a system and process for recovering high-quality biomethane and carbon dioxide product streams from biogas sources and utilizing or sequestering the product streams. The system and process improve upon conventional practices and yields a biomethane product which meets strict gas pipeline quality specifications and a carbon dioxide product of a quality and form that allows for its sequestration or utilization and reduction in greenhouse gas emissions. The system and process result in improved access to gas pipelines for products, an improvement in the carbon intensity rating of the biomethane fuel, and improvements in generation of carbon credits. Additionally, the system and process are an improvement to the overall methane recovery efficiency for biogas processing facilities. In certain illustrative embodiments, the system and process can involve aspects of: extraction of one or more gas streams comprising biogas from a biogas-generating facility; compression, cooling, and separation of liquid water; removal of a majority of the trace contaminants from the gas; removal of oxygen from the gas; drying the gas to further reduce the water vapor content; cooling the gas to liquefy at least some of the contained carbon dioxide; utilizing the liquid carbon dioxide as an absorbent to purify the gas stream; separating the remaining gaseous carbon dioxide from the gas stream and recycling the gaseous carbon dioxide to a point upstream from the liquefaction unit such that carbon dioxide contained in the biogas stream is substantially separated as a liquid product; separating nitrogen from the gas stream; sequestering or supplying the biogas-derived carbon dioxide for sequestration or other utilization; utilizing or supplying the biomethane as compressed or liquefied fuel for vehicles, as process heat fuel, as feedstock for fuel or chemical synthesis, or as feedstock for hydrogen generation; and monitoring the material and energy inputs and outputs from the biogas processing facility to verify reductions in greenhouse gas emissions. As used herein, the phrase "biogas processing facility" shall not be limited to simply a single building, plant or other like facility, but shall also mean any collection of such buildings, plants or facilities as used to accomplish the subject matter described herein.

The majority of biomethane recovery processes for gas pipeline injection applications utilize PSA processes, membranes, or physical solvents, or some combination thereof, but these processes and technologies have shown certain limitations. While the purified biomethane product from conventional processes may not consistently meet the most stringent specifications for pipeline tariff gas quality parameters, the presently disclosed subject matter satisfies all known requirements (Tables 1 and 2).

TABLE 1

Common gas quality parameters and modeled values based on an illustrative embodiment of this presently disclosed subject matter.

| Parameter | An illustrative embodiment |
| --- | --- |
| Gross Heating Value, BTU/SCF | >1006 |
| Wobbe Number, BTU/SCF | >1348 |
| Hydrocarbon Dew Point, deg F | <−100 |
| Water Vapor, lb/MMSCF | <1 |
| Total Sulfur, grains per 100 SCF | <0.1 |
| Hydrogen Sulfide, grains per 100 SCF | <0.1 |
| Diluents/Inerts, vol % | <0.5 |
| Carbon Dioxide, vol % | <0.002 |
| Oxygen, vol % | <0.001 |
| Nitrogen, vol % | <0.5 |

TABLE 2

Less common gas quality parameters and modeled values based on an illustrative embodiment of this presently disclosed subject matter.

| Parameter | An illustrative embodiment |
| --- | --- |
| Hydrogen, vol % | <0.001 |

TABLE 2-continued

Less common gas quality parameters and modeled values based on an illustrative embodiment of this presently disclosed subject matter.

| Parameter | An illustrative embodiment |
|---|---|
| Carbon Monoxide, vol % | <0.001 |
| Siloxa nes, mg Si/m3 | <0.01 |
| Halocarbons, ppmv | <0.1 |
| Mercury, mg/m3 | <0.01 |
| Arsenic, mg/m3 | <0.01 |
| Antimony, mg/m3 | <0.01 |
| Copper, mg/m3 | <0.01 |
| Lead, mg/m3 | <0.01 |

TABLE 2-continued

Less common gas quality parameters and modeled values based on an illustrative embodiment of this presently disclosed subject matter.

| Parameter | An illustrative embodiment |
|---|---|
| Other Volatile Metals, mg/m3 | <0.01 |
| p-Dichlorobenzenes, mg/m3 | <0.1 |
| Ethyl benzene, mg/m3 | <0.1 |
| n-Nitroso-di-n-propylamine, mg/m3 | <0.01 |
| Vinyl Chloride, mg/m3 | <0.1 |
| Ammonia, vol % | <0.001 |
| Methacrolein, ppmv | <0.1 |
| Toluene, ppmv | <0.1 |
| AlkyThiols (mercaptans), ppmv | <1 |
| Semi-Volatile and Volatile Compounds, ppmv | <0.1 |
| Aldehyde/Ketones, ppmv | <0.1 |

The conventional PSA, membrane, and physical solvent-based approaches are also typically limited to methane recovery of less than 97% (Table 3). Additionally, the conventional methods of biogas processing yield a contaminant-laden carbon dioxide off-gas at low pressure with little applicability, so the carbon dioxide is typically emitted to atmosphere. Due to the lack of carbon dioxide capture and sequestration or utilization, the biomethane product suffers from moderate carbon intensity ratings, typically in the range of 30-60 $gCO_2e/MJ$ for bio-CNG applications as compared to the baseline of about 100 $gCO_2e/MJ$ for petroleum-derived diesel or gasoline vehicle fuel (Table 4). The presently disclosed subject matter simultaneously and synergistically improves upon these limitations and comprises a system and process which ensures that the biomethane product meets all pipeline gas quality specifications for any reasonable range of biogas feed conditions while also improving the methane recovery and carbon intensity rating for the biomethane fuel due to capture and utilization or sequestration of the carbon dioxide. By utilizing or sequestering the carbon dioxide and improving the carbon intensity of the biomethane fuel, improved access and value is gained in markets such as California and Oregon's LCFS markets, European markets, and the IRS 45Q tax credit for carbon oxide sequestration, which significantly improves revenue opportunity.

TABLE 3

Product recovery efficiencies for conventional processes versus an illustrative embodiment of the presently disclosed subject matter.

| | | Conventional biogas processing facilities | | | | An illustrative embodiment |
|---|---|---|---|---|---|---|
| Process description | | Case 1 | Case 2 | Case 3 | Case 4 | Case 5 |
| NMOC removal | | PSA, activated carbon | PSA, activated carbon | Selexol absorber | Selexol absorber | ISA, $CO_2$ absorber |
| $CO_2$ removal | | Membranes | Membranes, amine absorber | Selexol absorber | Selexol absorber amine absorber | $CO_2$ liquefaction, membranes, amine absorber |
| $O_2$ removal | | Membranes, PSA | Membranes, $O_2$ converter | $O_2$ converter | $O_2$ converter | $O_2$ converter |
| $N_2$ removal | | PSA | Cryogenic Product recovery | PSA | Cryogenic | Cryogenic |
| $CH_4$ | % | 95.9 | 96.2 | 95.8 | 96.4 | 98.5 |
| $CO_2$ | $gCO_2/MJ$ | 0.0 | 0.0 | 0.0 | 0.0 | 39.3 |

Conventional methods of biogas processing for methane recovery involve separating and emitting the carbon dioxide contained in the biogas. This presently disclosed subject matter includes recovery of the carbon dioxide for utilization or sequestration to substantially reduce emissions of carbon dioxide associated with the biomethane recovery process and resultingly generate credits from the sequestration, utilization, and/or reduction in fuel carbon intensity. Process models and simulations were constructed using VMGSim with appropriate thermodynamic packages and equations of state to compare process efficiencies for conventional biogas processing facilities versus the presently disclosed subject matter. For a baseline scenario where carbon dioxide emissions from electricity generation are at the 2014 US average levels of 610 $gCO_2e/kWh$ and the biomethane product is transported via pipeline 2,000 miles to a CNG fueling station, conventional landfill biomethane recovery processes have carbon intensities of roughly 41-48 $gCO_2/MJ$ versus approximately 5 $gCO_2e/MJ$ for the preferred embodiment (Table 4). At $100/ton $CO_2$ credit price, the equivalent credit or fuel premium value for the baseline processes with carbon intensities of 41-48 $gCO_2e/MJ$ ranges from $3.9-4.6/mmbtu. Under the preferred embodiment with carbon intensity of approximately 5 $gCO_2e/MJ$, the credit or fuel premium values are equivalent to $8.3/mmbtu at $100/ton $CO_2$ credit price, or approximately twice the value as credits from conventional processes. For a moderate-scale 2,000 mmbtu/d biomethane facility, the increase in revenue due to the improved credit or fuel premium value results in an increase of approximately $3 million/year at $100/ton $CO_2$ credit price as compared to the conventional processes of biomethane recovery from biogas. Revenue may also be generated through sale of the physical carbon dioxide product for use in enhanced oil recovery or other industrial use which displaces use of geologically stored carbon dioxide.

nitrogen to less than 0.5% in the methane gas and achieves a GHV of greater than 1,000 Btu/SCF, meeting all US pipeline gas quality specifications for carbon dioxide, nitrogen, total inert gases, heating value, and Wobbe Number (Table 1). Conventional methods of methane recovery from biogas can leave minor amounts of oxygen, hydrogen, and

TABLE 4

Comparison of carbon intensities for conventional biomethane recovery and utilization processes versus the preferred embodiment of the presently disclosed subject matter.

| Carbon Intensity | | Conventional biogas processing facilities | | | | An illustrative embodiment |
|---|---|---|---|---|---|---|
| | | Case 1 | Case 2 | Case 3 | Case 4 | Case 5 |
| Base RNG process | | | | | | |
| Feedstock processing | | | | | | |
| Biogas extraction impact | gCO2e/MJ | 0.78 | 0.78 | 0.78 | 0.78 | 0.78 |
| Grid electricity factor | gCO2e/kWh | 610.34 | 610.34 | 610.34 | 610.34 | 610.34 |
| Grid electricity impact | gCO2e/MJ | 18.87 | 14.30 | 20.67 | 14.09 | 18.29 |
| Natural gas factor | gCO2e/mmbtu LHV | 74,655 | 74,655 | 74,655 | 74,655 | 74,655 |
| Natural gas impact | gCO2e/MJ | 3.93 | 4.56 | 4.99 | 5.43 | 0.99 |
| Fugitive emissions factor | Fraction | 0.01 | 0.01 | 0.01 | 0.01 | 0.01 |
| Fugitive emissions impact | gCO2e/MJ | 4.61 | 4.59 | 4.66 | 4.59 | 4.52 |
| Subtotal | gCO2e/MJ | 28.19 | 24.23 | 31.10 | 24.89 | 24.60 |
| Gas transmission | | | | | | |
| Distance | miles | 2,000 | 2,000 | 2,000 | 2,000 | 2,000 |
| Pipeline emissions factor | gCO2e/mmbtu-mile | 4.08 | 4.08 | 4.08 | 4.08 | 4.08 |
| Pipeline emissions impact | gCO2e/MJ | 6.98 | 6.98 | 6.98 | 6.98 | 6.98 |
| Leakage factor | gCO2e/mmbtu-mile | 1.72 | 1.72 | 1.72 | 1.72 | 1.72 |
| Leakage impact | gCO2e/MJ | 2.94 | 2.94 | 2.94 | 2.94 | 2.94 |
| Subtotal | gCO2e/MJ | 9.93 | 9.93 | 9.93 | 9.93 | 9.93 |
| CNG use | | | | | | |
| CNG compression impact | gCO2e/MJ | 3.18 | 3.18 | 3.18 | 3.18 | 3.18 |
| Tailpipe emissions impact | gCO2e/MJ | 3.66 | 3.66 | 3.66 | 3.66 | 3.66 |
| Subtotal | gCO2e/MJ | 6.84 | 6.84 | 6.84 | 6.84 | 6.84 |
| Subtotal | gCO2e/MJ | 44.96 | 41.00 | 47.87 | 41.66 | 41.36 |
| CO2 recovery process | | | | | | |
| CO2 capture | | | | | | |
| CO2 emissions avoided | gCO2/MJ | N/A | N/A | N/A | N/A | 39 |
| CO2 transport | | | | | | |
| Distance | miles | N/A | N/A | N/A | N/A | 100 |
| Trailer capacity | Tonnes/trailer | N/A | N/A | N/A | N/A | 19 |
| Truck fuel efficiency | miles per gallon | N/A | N/A | N/A | N/A | 4.00 |
| Fuel emissions factor | gCO2e/gal | N/A | N/A | N/A | N/A | 12,628 |
| Fuel emissions impact | gCO2e/MJ | N/A | N/A | N/A | N/A | 1.31 |
| CO2 injection | | | | | | |
| Pumping electric factor | kWh/ton | N/A | N/A | N/A | N/A | 2.00 |
| Grid electricity factor | gCO2e/kWh | N/A | N/A | N/A | N/A | 610.34 |
| Grid electricity impact | gCO2e/MJ | N/A | N/A | N/A | N/A | 0.05 |
| Recovery | fraction | N/A | N/A | N/A | N/A | 0.95 |
| Subtotal | gCO2e/MJ | N/A | N/A | N/A | N/A | −36.06 |
| Total | gCO2e/MJ | 44.96 | 41.00 | 47.87 | 41.66 | 5.31 |

Conventional methods of biomethane recovery from biogas can leave trace amounts of halogenated compounds and siloxanes with the methane stream which can limit injection into pipelines due to pipeline quality standards. The presently disclosed subject matter involves removal of siloxanes to less than 0.01 mg Si/m3 and removal of halogenated compounds to less than 0.1 ppmv, meeting any current pipeline specification (Tables 1 and 2). Conventional methods of methane recovery from biogas can leave minor amounts of carbon dioxide and nitrogen with the methane stream which can limit injection into pipelines due to pipeline quality standards for inert gases or heating value. The preferred embodiment removes carbon dioxide and carbon monoxide with the methane stream which can limit injection into pipelines due to pipeline quality standards for oxygen, hydrogen, or carbon monoxide. The preferred embodiments involve removing all oxygen, hydrogen, and carbon monoxide, meeting all known pipeline specifications for oxygen, hydrogen, and carbon monoxide (Tables 1 and 2).

Figure 1:
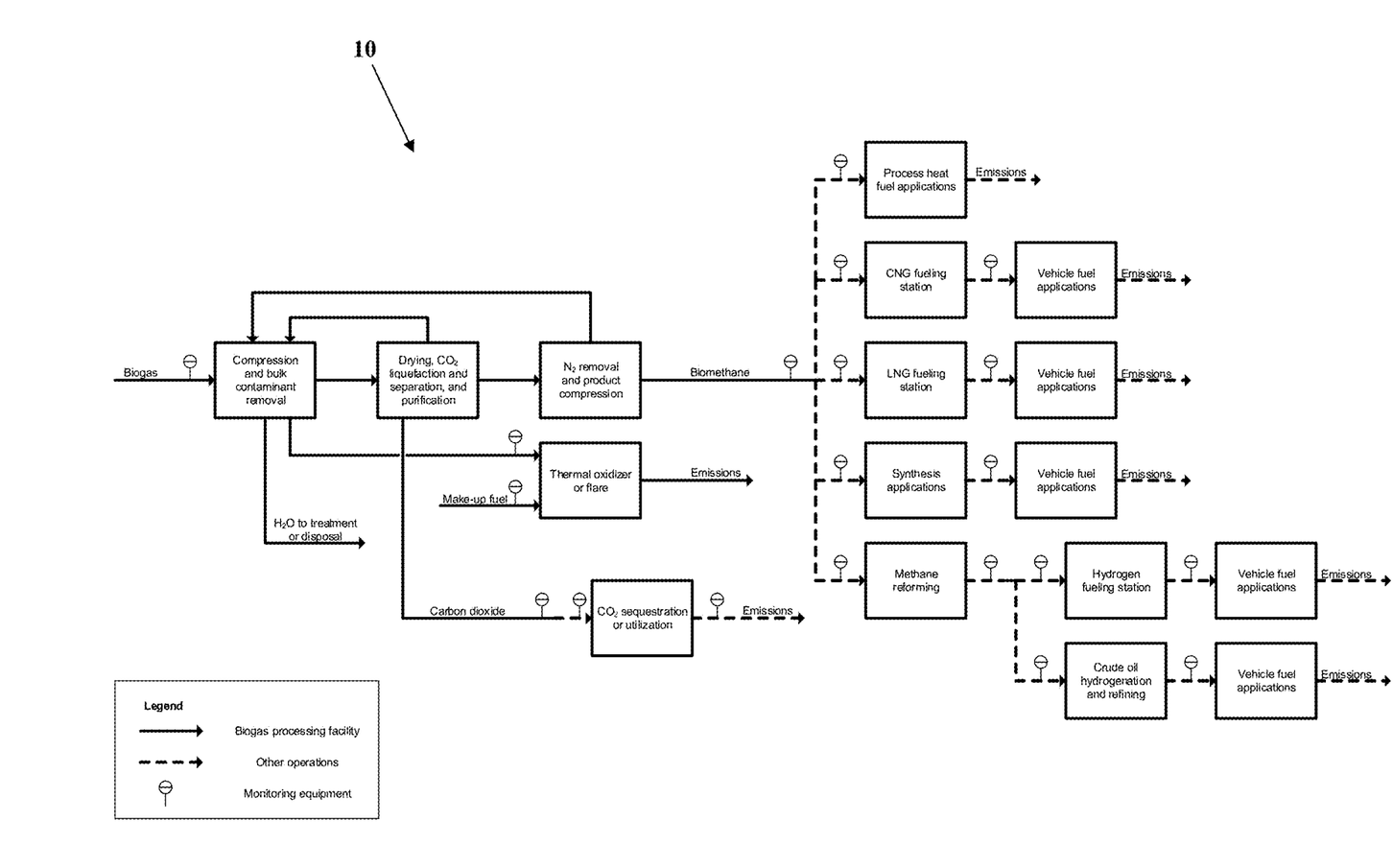
FIG. 1 is an example of a system and process for recovering biomethane and carbon dioxide product streams from biogas sources and utilizing or sequestering the product streams in accordance with an illustrative embodiment of the presently disclosed subject matter.

An illustrative embodiment of the presently disclosed system and process 10 is shown in FIG. 1. FIG. 1 illustrates an exemplary system and process 10 with a plurality of sequential, non-sequential, or sequence independent "steps" using the equipment shown or described herein. It should be noted that the system and process 10 of FIG. 1 is exemplary, and may be performed in different orders and/or sequences as dictated or permitted by the equipment described herein, and any alternative embodiments thereof. Other arrangements of the various "steps" and equipment can be utilized. In addition, not all "steps" or equipment described herein need be utilized in all embodiments. However, it should be noted that certain particular arrangements of equipment and/or "steps" for the system and process 10 such as shown in FIG. 1 are preferred embodiments, and are materially distinguishable from and provide distinct advantages over previously known technologies.

Extraction of Biogas

In certain illustrative embodiments, biogas is extracted from a biogas generating facility through conventional methods. If the biogas generating facility is a solid waste landfill, the biogas is extracted via a blower which pulls a slight vacuum on a gas collection system. If hydrogen sulfide, hydrogen and/or carbon monoxide are contained in the biogas, oxygen can be drawn in from atmosphere along with the biogas at a ratio of at least 0.5 moles oxygen to moles hydrogen sulfide, hydrogen, and carbon monoxide to facilitate removal of hydrogen sulfide, hydrogen, and carbon monoxide downstream.

Compression, Cooling, and Separation of Water

In certain illustrative embodiments, biogas is compressed, cooled, and separated from liquid water using conventional methods. In the preferred embodiment, biogas is compressed to about 5-15 psig, cooled in an air-cooled heat exchanger to around ambient dry bulb temperature or in a water-cooled heat exchanger to around ambient wet bulb temperature, and separated from liquid water.

Removal of the Majority of the Trace Contaminants and Oxygen

In certain illustrative embodiments, hydrogen sulfide is removed from the biogas using conventional means such as through adsorption on activated carbon, reaction with iron oxide based media, or absorption in a wet scrubber. The hydrogen sulfide may also be removed from the biogas via less conventional means, such as through oxidation to sulfur dioxide and wet scrubbing of the sulfur dioxide. Depending on the method of removing hydrogen sulfide, the humidity, temperature, and oxygen level in the feed gas are controlled to provide optimal conditions for the hydrogen sulfide removal process. For example, for hydrogen sulfide removal on specialized activated carbon or iron oxide media, the oxygen level should be controlled to at least 0.5 moles oxygen per mole hydrogen sulfide to facilitate conversion to elemental sulfur. For hydrogen sulfide removal through oxidation to sulfur dioxide, the oxygen in the feed should be controlled to at least 1.5 moles oxygen per mole hydrogen sulfide.

In certain illustrative embodiments, following removal of hydrogen sulfide, the biogas is compressed to about 90-150 psig, cooled in a manner similar to the first stage, and separated from any liquid. The biogas is compressed further to between about 250-700 psig, cooled in a manner similar to the first stage, and separated from any condensed liquid. In certain illustrative embodiments, the compressed biogas is separated from the bulk of the minor contaminants, including organic sulfides, halogenated hydrocarbons, siloxanes, semi-volatile and volatile organic compounds, and volatile metals using a PSA or TSA process. The majority of the contaminants may alternatively be removed via a physical solvent absorber, but the preferred approach is a TSA. The adsorbents consist of media with known affinity for adsorption of the majority of landfill gas contaminants, such as activated carbon, promoted activated carbon, silica gel, molecular sieves, or some combination. The spent beds are regenerated by flowing nitrogen that has been separated from the gas through the spent bed at a pressure lower than adsorption pressure and, preferably, higher than adsorption temperature. Preferably, the nitrogen flows through the bed at a pressure between 1-10 psig and at a temperature between 300-800 deg F. and is then routed to a thermal oxidizer or flare for thermal destruction of the separated contaminants. A single vessel or lead-lag arrangement of promoted or unpromoted activated carbon bed may be placed downstream from the PSA or TSA to help polish the gas.

The physical adsorbents are efficient at removing the bulk of the contaminants, particularly contaminants with relatively high boiling points. However, low boiling compounds, including some halogenated hydrocarbons, have very low adsorption tendencies and are not typically completely removed. Chloromethane for example, has very minimal loading on activated carbon. Therefore, in order to avoid extremely large and costly physical adsorbent systems, it is advantageous to allow the most difficult to adsorb contaminants, such as low boiling halogenated hydrocarbons, to pass through the physical adsorbents and instead remove them downstream in the carbon dioxide liquefaction process.

In certain illustrative embodiments, following removal of the bulk of the minor contaminants through adsorption, the gas may be transmitted to a catalytic oxidation reactor. The catalytic oxidation reactor may alternatively be placed in a variety of different locations in the process, but, in the preferred embodiment, the reactor is placed downstream from the bulk contaminant removal by adsorption to minimize poisoning and prolong the lifetime of the oxidation catalyst. The reactor utilizes platinum group metal catalysts to catalyze the oxidation of hydrogen, carbon monoxide, and residual reactive VOC's to simultaneously remove the hydrogen, carbon monoxide, VOC's, and oxygen. The oxygen level in the feed gas can be maintained at minimum of 0.5 moles oxygen to moles hydrogen and carbon monoxide by controlling the vacuum or air intrusion into the biogas. If necessary, an easily reactive chemical, such as methanol, can be injected into the feed stream to facilitate and complete the removal of oxygen. The catalytic oxidation reactor preferably operates at a temperature less than 575 deg F. Alternatively, the reactor may be operated at temperatures greater than 575 deg F. to facilitate removal of oxygen by oxidation of methane, but this is less desirable.

Drying the Gas Stream

In certain illustrative embodiments, the gas stream is then dried using convention technology, such as molecular sieve, silica gel, or triethylene glycol dryer. In the preferred embodiment, the gas is dried with a molecular sieve drier to a moisture dew point temperature of less than −40 deg F., and the spent beds are regenerated by flowing a portion of the dried gas back through the spent bed at an elevated temperature between about 300-500 deg F. The regeneration steam is cooled and recycled to a point upstream the previous compression stage.

Carbon Dioxide Liquefaction and Utilization as an Absorbent to Purify the Gas Stream Following drying, in certain illustrative embodiments the gas is cooled to liquefy a portion of the contained carbon dioxide such that carbon dioxide may be separated from the gas stream as a liquid. In the preferred embodiment, the dried gas is first pre-cooled to less than 50 deg F. before being fed to refluxed absorber column. The overhead gas stream from the column is transmitted to a cooler or condenser where the gas is cooled to a point where a portion of the contained carbon dioxide condenses as liquid. Preferably, the gas is cooled to a temperature between −25 and −75 deg F. The gas and the liquid carbon dioxide stream are separated, and the liquid carbon dioxide is transmitted back to the upper section absorber column as reflux. As the liquid carbon dioxide travels down the column, the liquid carbon dioxide absorbs contaminants from the feed stream. As result, the overhead gas stream is purified from contaminants (Table 5). The bottoms product stream is primarily composed of liquid carbon dioxide as well as a small amount of methane and any absorbed contaminants that had passed through the upstream bulk contaminant removal process. In the preferred embodiment, the pressure of the bottom product stream is reduced such that a portion of the stream is vaporized, including most of the methane that was contained in the liquid carbon dioxide stream. The methane-rich vapor is then recycled to a point upstream the previous compression stage.

As an alternative to using of an absorber tower, the gas stream may simply be cooled to the point at which carbon dioxide condenses as liquid which is then separated from the vapor stream in a two-phase separator. However, the potential for reduction of contaminant levels in the gas stream is reduced in this embodiment. The method which involves an absorber column has the advantages of ensuring a purified gas stream is produced as well as the advantage that the feed gas warms the liquid carbon dioxide as the two streams become in contact, which allows for immediate flashing of the bottoms stream for methane recovery and recycle.

from the previous compression stage. As a result, the carbon dioxide contained in the biogas is substantially separated and recovered as a liquid product.

Separating Nitrogen from the Biogas

In certain illustrative embodiments, the gas stream which has been separated from carbon dioxide is further dried and sent to a nitrogen removal unit for separation of nitrogen using conventional technology. The nitrogen removal unit may be composed of membranes, a PSA which preferentially adsorbs methane, a PSA which preferentially adsorbs nitrogen, or a cryogenic separation unit. In the preferred embodiment, the nitrogen is separated in a single or double column cryogenic separation process. If necessary, the pressure of the gas stream is first boosted via compression, then the gas is pre-cooled and let down in pressure via a Joule-Thomson valve to cool the gas to the point at which a portion of the methane is condensed as liquid and then fed to a cryogenic distillation column. Liquefied methane is withdrawn as a bottom stream from the column, and enriched nitrogen is withdrawn as an overhead vapor stream. The overhead nitrogen-rich vapor stream is cooled further and let down in pressure via another Joule-Thomson valve to cool further and condense a portion of the stream. The stream is then fed to a reboiled absorber column which further separates the nitrogen and methane such that the overhead stream consists primarily of nitrogen with less than one percent methane, and the bottoms stream consists primarily of liquified methane stream.

In the preferred embodiment, the overhead nitrogen stream is heated and sent to the TSA where the bulk of the

TABLE 5

Fate of representative contaminants fed to the carbon dioxide liquefaction and absorber unit at inlet concentration of 1 ppmv.

| Contaminant | Molecular weight | Concentration in feed gas | Contaminant in biomethane product | | Contaminant in carbon dioxide product | |
|---|---|---|---|---|---|---|
| Halogenated methanes: | g/mol | mol frac | mol frac | % removed | mol frac | % absorbed |
| Chloromethane | 50.49 | 1.0E+00 | 1.0E−100 | 100 | 2.5E−06 | 100 |
| Dichloromethane | 84.93 | 1.0E−06 | 1.0E−100 | 100 | 2.5E−06 | 100 |
| Trichloromethane | 119.38 | 1.0E−06 | 1.0E−100 | 100 | 2.5E−06 | 100 |
| Tetrachloromethane | 153.82 | 1.0E−06 | 1.0E−100 | 100 | 2.5E−06 | 100 |
| Chlorofluoromethane | 68.48 | 1.0E−06 | 1.0E−100 | 100 | 2.5E−06 | 100 |
| Chlorodifluoromethane | 86.47 | 1.0E−06 | 6.4E−13 | 100 | 2.5E−06 | 100 |
| Dichlorofluoromethane | 102.92 | 1.0E−06 | 1.0E−100 | 100 | 2.5E−06 | 100 |
| Dichlorodifluoromethane | 120.91 | 1.0E−06 | 1.1E−11 | 100 | 2.5E−06 | 100 |
| Trichlorofluoromethane | 137.37 | 1.0E−06 | 1.0E−100 | 100 | 2.5E−06 | 100 |

Separating the Remaining Gaseous Carbon Dioxide from the Gas Stream

In certain illustrative embodiments, the purified gas stream is sent to additional separation equipment to separate the remaining gaseous carbon dioxide from the gas stream. The carbon dioxide may be separated from the gas using conventional methods, such as through PSA, membranes, use of physical solvents, use of chemical solvents, or some combination. In the preferred embodiment, the enriched biomethane from the liquefaction unit is sent to a membrane package, which reduces the carbon dioxide level to less than about 5 percent, then to an amine absorber to polish the carbon dioxide level to less than about 50 ppm. The permeate from the membrane is recycled to a point upstream from the previous compression stage. The rich amine solution from the amine absorber is flashed and sent to a regenerator tower to separate the carbon dioxide from the amine solution and allow recycle of the carbon dioxide to a point upstream contaminants are desorbed from a spent bed into the nitrogen stream and routed to a thermal oxidizer or flare for thermal destruction of the contaminants. The liquified biomethane streams are heated, combined, and recompressed to desired delivery pressure from the biogas processing facility. In the preferred embodiment, the heating and cooling requirements of the cryogenic nitrogen removal process are combined such that no external refrigeration is required. However, for liquefied natural gas (LNG) applications, external refrigeration may be used and the liquefied biomethane may be left in liquid form and pumped to desired delivery pressure. The biomethane product stream from the nitrogen removal unit contains less than 0.5% nitrogen and contains greater than 98% of the methane delivered to the biogas processing facility.

Thermal Oxidation or Flaring of Waste Gases

In certain illustrative embodiments, the separated nitrogen stream is sent to the TSA to regenerate an adsorbent bed which is saturated with contaminants. The contaminants are desorbed from the saturated bed into the nitrogen stream and routed to a thermal oxidizer, regenerative thermal oxidizer, or flare for thermal destruction of the contaminants. If a physical solvent is alternatively used for bulk contaminant removal, the nitrogen may be used to strip the solvent from contaminants and routed to the thermal oxidizer or flare for thermal destruction of the contaminants. The presently disclosed subject matter results in a reduced fuel load on the thermal oxidizer due primarily to the fact that the carbon dioxide is not routed to the thermal oxidizer. This not only results in fuel gas savings, but an improved carbon intensity rating for the biomethane fuel and improved generation of credits.

Sequestering or Utilizing the Carbon Dioxide

In certain illustrative embodiments, the carbon dioxide separated from the biogas is sequestered or utilized in a manner which isolates or displaces emissions of carbon dioxide. The carbon dioxide may be sequestered through use in enhanced oil recovery, injected into secure geologic formations, injected into deep marine sediments, or reacted with certain rocks and minerals to form stable carbonates. The carbon dioxide may alternatively be utilized as feedstock in chemical or fuel synthesis, as an industrial refrigerant, or in the food and beverage industry in a manner which avoids extraction of geologic carbon dioxide and reduces emissions. The sequestration or utilization may occur on site, or the carbon dioxide may be supplied to another party and transported via truck, rail, barge or pipeline to another facility for sequestration or utilization. The carbon dioxide may be pumped to reach required delivery pressure and heated as needed to meet particular temperature requirements for transport, sequestration, or utilization. In the preferred embodiment, the carbon dioxide is supplied to another party and transported via truck or pipeline to another facility to be injected underground into a suitable geologic formation for permanent storage.

Utilizing the Biomethane

In certain illustrative embodiments, the biomethane product is utilized as compressed or liquefied fuel for vehicles, as feedstock for synthesis of chemicals or fuels, or as process heat fuel. The gas may be utilized on site or sold and transported via pipeline, truck, barge, or rail to an off-site CNG or LNG fueling station for use as a vehicle fuel or to another facility for use as process heat fuel. The biomethane may also be used as feedstock in a fuels or chemicals synthesis facility to generate renewable diesel, renewable gasoline, biomethanol, or bioethanol. The biomethane may also be reformed to generate hydrogen for use in petroleum refining or in vehicle fuel applications.

Monitoring Feedstock Usage, Production, and Emissions

In certain illustrative embodiments, the material and energy inputs and outputs from the facility are monitored to verify reductions in emissions of greenhouse gases associated with the biogas processing. The flow rate and composition of the biogas feedstock is monitored, as well as any process heat fuel usage and electricity usage. The production and composition of the biomethane and carbon dioxide products are monitored, and the off-gas to the thermal oxidizer or flare may be monitored as well to close the material and energy balance and verify reductions in emissions of greenhouse gases.

In accordance with the presently disclosed subject matter, when there is a desire or need for high pressure carbon dioxide, such as when carbon dioxide is transported via pipeline or injected underground for in enhanced oil recovery or geologic storage, it is most efficient to separate carbon dioxide via low temperature fractionation or liquefaction as opposed to conventional means of separation due to the fact that much less power is required to pump liquid carbon dioxide up to delivery pressure than is required to compress gaseous carbon dioxide up to required delivery pressure. Similarly, when there is a need for liquid carbon dioxide, such as when transported via truck, rail, or barge, it is most efficient to separate the carbon dioxide as a liquid via low temperature fractionation or liquefaction. The presently disclosed system and process allow for separation of the carbon dioxide from the biogas in a relatively pure liquid form which is suitable for transport, utilization, or storage and enable significant reductions in overall greenhouse gas emissions and improvements in generation of associated credits. Accomplishing this feat while simultaneously and synergistically generating a purified biomethane product and improving the overall methane recovery efficiency of the process results in a significant improvement beyond current practices.

While the disclosed subject matter has been described in detail in connection with a number of embodiments, it is not limited to such disclosed embodiments. Rather, the disclosed subject matter can be modified to incorporate any number of variations, alterations, substitutions or equivalent arrangements not heretofore described, but which are commensurate with the scope of the disclosed subject matter.

Additionally, while various embodiments of the disclosed subject matter have been described, it is to be understood that aspects of the disclosed subject matter may include only some of the described embodiments. Accordingly, the disclosed subject matter is not to be seen as limited by the foregoing description, but is only limited by the scope of the claims.

What is claimed is:

1. A process for recovering methane and carbon dioxide from a biogas source for beneficial use or sequestration, comprising the steps of:
   (a) extracting at least one gas stream comprising a biogas from a biogas-generating facility;
   (b) compressing, cooling, and separating the gas stream from liquid water;
   (c) removing a majority of trace contaminants from the gas stream;
   (d) cooling the gas stream in a liquefaction unit to liquefy at least some of the contained carbon dioxide;
   (e) separating remaining gaseous carbon dioxide from the gas stream and recycling to a point upstream from the liquefaction unit such that the carbon dioxide is substantially recovered as a liquid product;
   (f) recovering a biomethane product from the gas stream for beneficial use;
   (g) monitoring material and energy inputs and outputs from a biogas processing facility, wherein at least some of steps (b)-(f) occur in the biogas processing facility.

2. The process of claim 1, including any of the additional steps of:
   (a) removing oxygen from the gas stream to produce a deoxygenated gas stream;
   (b) drying the gas stream to reduce the water vapor content;
   (c) utilizing the liquified carbon dioxide as an absorbent to purify the gas stream;
   (d) separating nitrogen from the gas stream;
   (e) sequestering or supplying the carbon dioxide product for sequestration or other utilization; or
   (f) utilizing or supplying the biomethane product stream as a compressed or liquefied fuel for vehicles, as process heat fuel, as feedstock for fuel or chemical synthesis, or as feedstock for hydrogen generation.

3. The process of claim 2, including the further step of utilizing the separated nitrogen stream to regenerate contaminant-laden adsorbent or absorbent.

4. The process of claim 3, including the further step of transmitting the contaminant-laden nitrogen stream to a thermal oxidizer or flare for thermal destruction of the contaminants.

5. The process of claim 2, wherein the carbon dioxide is sequestered through injection into an underground geologic reservoir for permanent storage or reacted with another material to form carbonate minerals.

6. The process of claim 5, including the additional step of monitoring the reservoir for verification of extended or permanent storage of carbon dioxide or monitoring the conversion of carbon dioxide to carbonate minerals for verification of sequestration.

7. The process of claim 1, wherein air intrusion into the biogas is controlled to achieve a minimum oxygen to hydrogen, carbon monoxide, and hydrogen sulfide ratio of 0.5.

8. The process of claim 1, wherein the overall methane recovery efficiency is greater than 98%.

9. The process of claim 1, wherein the gross heating value of the biomethane product stream is greater than 1,000 Btu/SCF.

10. The process of claim 1, wherein the carbon intensity of the biomethane product stream is less than 25 $gCO_2e/MJ$.

11. The process of claim 1, wherein the halogenated hydrocarbon level in the biomethane product stream is less than 0.1 ppmv.

12. The process of claim 1, wherein the siloxane level in the biomethane product stream is less than 0.01 mg $Si/m^3$.

13. The process of claim 1, wherein credits are generated due to the reduction in emissions of greenhouse gases.

* * * * *